(12) United States Patent
Motoki

(10) Patent No.: US 7,769,602 B2
(45) Date of Patent: Aug. 3, 2010

(54) MEDICAL IMAGE CREATING SYSTEM, MEDICAL IMAGE CREATING METHOD AND DISPLAY CONTROLLING PROGRAM

(75) Inventor: Wataru Motoki, Hachioji (JP)

(73) Assignee: Konica Minolta Medical & Graphic, Inc., Tokya (JP)

( * ) Notice: Subject to any disclaimer, the term of this patent is extended or adjusted under 35 U.S.C. 154(b) by 1128 days.

(21) Appl. No.: 11/091,125

(22) Filed: Mar. 28, 2005

(65) Prior Publication Data

US 2005/0222871 A1    Oct. 6, 2005

(30) Foreign Application Priority Data

Apr. 6, 2004    (JP) .............................. 2004-112356

(51) Int. Cl.
*A61B 5/00* (2006.01)
*G06F 19/00* (2006.01)
(52) U.S. Cl. ......................................................... 705/3
(58) Field of Classification Search ...................... 705/2, 705/4; 250/584; 345/810; 382/128; 600/437
See application file for complete search history.

(56) References Cited

U.S. PATENT DOCUMENTS 6,500,118 B1 * 12/2002 Hashimoto .................. 600/437
2001/0011713 A1 * 8/2001 Nagatsuka et al. .......... 250/584

* cited by examiner

*Primary Examiner*—Gerald J. O'Connor
*Assistant Examiner*—John A Pauls
(74) *Attorney, Agent, or Firm*—Lucas & Mercanti, LLP

(57) ABSTRACT

In a controller which controls a reader for reading a radiographic image recorded in a cassette, a display controlling device is provided for the user to select one of three modes. The three modes are a pre-registration, a post-registration mode, and a non-registration mode. In the pre-registration mode, radiographing is conducted to acquire an image after the relationship between information of the body part to be radiographed and the cassette has been registered as radiographing reservation information. In the post-registration mode, an image is acquired after the relationship between information of the body part to be radiographed and the cassette insertion order has been registered as radiographing reservation information. In the non-registration mode, an image is acquired without registration of any relationship as radiographing reservation information and the following processes are continued according to the user's selected mode.

16 Claims, 13 Drawing Sheets

MEDICAL IMAGE CREATING SYSTEM, MEDICAL IMAGE CREATING METHOD AND DISPLAY CONTROLLING PROGRAM

This application is based on Japanese Patent Application No. 2004-112356 filed on Apr. 6, 2004 in Japanese Patent Office, the entire content of which is hereby incorporated by reference.

BACKGROUND OF THE INVENTION

The present invention relates to a medical image creating system, a medical image creating method and a display controlling program, whereby diagnosis is conducted by using a radiographic image acquired by radiographing a patient.

A radiographic image acquired by using radiation such as X-rays is widely employed as a medical image for disease diagnosis. For example, so-called radiography has been used in such a way that X-rays, transmitted through an examined body, are exposed to a phosphor layer (fluorescent screen). Then visible light generated from the phosphor layer is exposed to film employing silver salt and the film is developed, similar to an ordinary photograph.

However, recently, a radiographic image creating method by which a radiographic image is directly picked up as digital signals with a radiation detector such as stimulating phosphor or an FPD (Flat Panel Detector) without using a film coated with silver salt has been popular. Various kinds of image processing have been used for acquiring a radiographic image for medical diagnoses.

Specifically, for example, a radiographic image transduction method which transduces visible light or infrared light into stimulation light, is disclosed in U.S. Pat. No. 3,859,527 and Tokkai Shyou 55-12144. This method uses a radiographic image transduction plate having a stimulable phosphor layer on a support. The radiographic image transduction plate having a stimulable phosphor layer on a support has accumulated radioactive energy which is emitted as a stimulating light by scanning the stimulable phosphor layer with stimulating light such as a laser beam of a prescribed wavelength. The stimulating light is applied to the plate with photoelectric transformation by using a photoelectric transformation element such as a photomultiplier to pick out the emitted stimulating light as an electric signal. The radiation, which has been transmitted through an examined body part is accumulated in the stimulable phosphor layer and corresponds to the radiation transmittance amount of each part of the examined body.

The radiographic image diagnosis system known as computed radiography (CR) is generally divided into two systems. One is a system dedicated to patient's standing and lying positions in which a stimulable phosphor plate is installed in the reading apparatus, and the other is a cassette type system combining a portable cassette storing a stimulable phosphor plate inside and a reading apparatus (reader) which reads the data after removing the phosphor plate from the cassette. The cassette type system are disclosed in Tokkai Nos. 2002-159476 and 2002-158820 for example.

This cassette type radiographic image diagnosis system will now be explained referring to FIG. 16. As shown in FIG. 16, conventional cassette type radiographic diagnosis system 1 is composed of a plurality of examination rooms in each of which radiographing apparatus 4, which radiographs examined body part M, is installed; and an operation space where image reading apparatuses, readers 2, are installed. Each reader 2 reads radiographic image data from portable cassette 17, in which a radiographic image transduction plate is housed. Each cassette 17 incorporates stimulable phosphor sheet 18, which absorbs radiation energy. In each examination room, a controlling apparatus (controller 3) displays the radiographic image, input of patient information and body part information, as well as controlling reader 2. Further, reader 2, controller 3, job manager 19 and study manager 20 are connected as a LAN via switching hub 5.

In the examination room, a patient is positioned between radiation source 16 and cassette 17. When radiation is irradiated via radiation source 16, stimulable phosphor sheet 18 in cassette 17 absorbs and stores a part of the radiation energy. After radiographing, this cassette is brought to the operation space and is put into reader 2, and reader 2 irradiates excitation light to expose stimulable phosphor sheet 18 in cassette 17 so that stimulable phosphor sheet 18 emits stimulable light corresponding to radiographic image information stored on it. A photoelectric transduction is applied to the emitted stimulable light to output it as digital image data after A/D conversion.

Controller 3 has a display means for input of patient information or body part information and confirmation of the read image, as well as controls reading operation of reader 2. In this display means, for example, screens are displayed in an order, such as the reception list screen displaying a list of registered patients, the registration/search screen for registration of a new patient or for searching for patient information by inputting certain search data, the body part selection screen for setting the body part information for the selected patient, the image display screen displaying a radiographed image, or an image created by applying image processing to a radiographed image, so as to realize a work flow from reading to confirmation of images. If the desired image is not obtained, the system is structured so that the screen is switched to the image processing adjustment screen to change the image processing conditions used for image processing and an adjustment operation of image processing can be performed until the desired image is acquired.

[Patent Document 1] Tokkai No. 2002-159476
[Patent Document 2] Tokkai No. 2002-158820

A large hospital typically has a plurality of radiographing apparatuses 4, readers 2 and controllers 3, where a plurality of radiologists operate radiographing apparatuses 4 and a plurality of doctors can diagnose by using radiographic images acquired by radiographing various body parts of a plurality of patients. In order to clarify the correlation between body part information and cassette 17, preventing mistaken images for diagnoses, either of two modes is employed. One is a mode in which radiographing is carried out after correlation between body part information and cassette 17 is registered as radiographing reservation information (pre-registration mode). Another mode is one in which correlation between body part information and insertion order of cassette 17 is registered as radiographing reservation information without registration of cassette 17 before radiographing (post-registration mode).

In the pre-registration mode, an operator first reads an ID label applied on cassette 17, inputs patient information and/or body part information, wherein the inputted body part information and the ID label are correlated to each other. Then, X-ray radiographing is carried out by using the registered cassette 17. The cassette 17, where a latent image has been formed, is inserted into reader 2, which reads the ID label of cassette 17 and a set of body part information corresponding to this ID label, thereby acquiring reading conditions from the parameter set. Further, according to the acquired conditions, an image is read and is sent to controller 3 together with the cassette ID. Controller 3 correlates radiographing reservation information and the read image, employing cassette ID as a key, and displays the image after image processing according to the radiographing condition parameters.

In the post-registration mode, X-ray radiographing is carried out first and then, each inputted body part and the cassette insertion order are stored and correlated to each other. In addition, patient information or body part information are inputted. Cassette 17, where a latent image has been formed, is inserted into reader 2, which reads out body part information or the radiographing condition parameter set corresponding to the insertion order and acquires the reading conditions from the parameter set. Further, an image is read out according to the acquired reading conditions and sent to controller 3, which displays the image after conducting image processing according to the radiographing condition parameters.

The pre-registration mode and post-registration mode are effective methods in a large hospital. However, according to a survey of the inventors of this invention, in small medical practitioner's clinics, the number of operators for radiographing apparatus 4 is normally one or two, and radiographing of a plurality of body parts or a plurality of directions is seldom carried out. Further, the number of doctors who diagnose by using radiographic images is usually one or two, and still further, the number of radiographing apparatuses 4, readers 2 and controllers 3 is also small. Accordingly, it is unlikely that images are miscorrelated in a small medical practitioner's clinic, and therefore the above pre-registration mode or post-registration mode is sometimes inconvenient.

Specifically, in clinics of few medical practitioners, where the number of patients is few or radiographing demand is small at a time, it is easy to know which patient was radiographed, how many radiographs were taken and the image of which patient is being shown. It is therefore not critical to read the ID number on cassette 17 or to correlate the insertion order. It is usually sufficient to correlate patient information after displaying the read image or when the image is stored in a database. Accordingly, a system including modes which can be easily used by any scale of medical facility, whether a large hospital or a small medical practitioner's clinic is desired.

SUMMARY OF THE INVENTION

This invention was produced from the view point of the above-stated problems, and the major objective is to provide a medical image creating system, a medical image creating method and a display controlling programs which are convenient for users of various sized medical facilities, such as a large hospital as well as a smaller medical practitioner's clinic.

The above objective can be achieved by the following system, method and program.

(A) A medical image creating system, comprising: a recording medium to record a radiographic image obtained by radiographing a subject, a reading section to read the radiographic image recorded on the recording medium, and a controlling section to acquire the read radiographic image. The read radiographic image is correlated with an examination information including at least patient information, wherein the medical image creating system has a plurality of modes that is selectable by the controlling section. The selectable modes include a first mode, in which the examination information is correlated with the read radiographic image, by correlating the recording medium with the examination information before the reading section reads the radiographic image; and a second mode, in which at least one of the read radiographic images is acquired, and the acquired images are correlated with the examination information.

(B) A medical image creating system to create a medical image, comprising: a medical image creating section to create a medical image by radiographing a subject, and a controlling section to acquire the created medical image. The created medical image is correlated with an examination information including at least patient information, wherein the medical image creating system has modes selectable by the controlling section. The selectable modes include a first mode, in which the created medical image can be correlated with the examination information before the controlling section acquires the created medical image; and a second mode in which the created medical image can be correlated with the examination information after the controlling section acquires the created medical image.

(C) A medical image creating method to create a medical image of a subject, comprising steps of: recording a radiographic image obtained by radiographing a subject onto a recording medium; reading the radiographic image recorded on the recording medium; acquiring the read radiographic image and correlating the read radiographic image with an examination information, including at least patient information, wherein a mode can be selected among a plurality of modes. Such modes include a first mode, in which the examination information is correlated with the read radiographic image by correlating the recording medium with the examination information before the reading step; and a second mode, in which at least one of the read radiographic images is acquired and the acquired images are correlated with the examination information. The medical image is created according to a procedure prescribed by the selected mode among the plurality of modes.

(D) A medical image creating method to create a medical image, comprising steps of: creating a medical image obtained by radiographing a subject, acquiring the created medical image and correlating the created medical image with examination information including at least patient information, wherein a mode can be selected. Such modes include a first mode, in which the created medical image can be correlated with the examination information before the acquiring step, and a second mode, in which the created medical image can be correlated with the examination information after the acquiring step. The medical image is created according to a procedure prescribed by the selected mode.

(E) A display controlling program operated in a medical image creating system, comprising: a recording medium to record a radiographic image obtained by radiographing a subject, a reading section to read the radiographic image recorded on the recording medium, and a controlling section to acquire the read radiographic image where the read radiographic image is correlated with examination information, including at least patient information. The display controlling program functions as a display controlling means by displaying a plurality of modes. A mode can be selected from a first mode, in which the examination information is correlated with the read radiographic image by correlating the recording medium with the examination information before the reading section reads the radiographic image, and a second mode in which at least one of the read radiographic images is acquired, and the acquired images are correlated with the examination information.

(F) A display controlling program operated in a medical image creating system to create a medical image, comprising: a medical image creating section to create a medical image by radiographing a subject, and a controlling section to acquire the created medical image. The created medical image is correlated with examination information including at least patient information, wherein the display controlling program is allowed to function as a display controlling means to display modes to be selected. Such modes include a first mode, in which the created medical image can be correlated with the examination information before the controlling section acquires the created medical image and a second mode, in which the created medical image can be correlated with the examination information after the controlling section acquires the created medical image.

According to this invention, a user can select one of the three following modes on the display means of a controlling apparatus. In a first mode, radiographing is conducted after registration of correlation of body part information with a cassette as radiographing reservation information. In a second mode, correlation of body part information and a cassette insertion order is registered as radiographing reservation information. In a third mode, an image is acquired without registration of correlation as radiographing reservation information. Therefore, a system convenient for various kinds of users from a large hospital to a smaller medical practitioner's clinic can be established.

According to the medical image creating system, the medical image creating method and the display controlling program of this invention, a system can be established, which is easy to employ whether a large scale user, such a large hospital, or a small scale user, such a medical practitioner's clinic.

The reason for the easiness is that, in addition to a pre-registration mode, where radiographing is conducted to acquire an image after correlation between body part information, a cassette is registered as radiographing reservation information, and a post-registration mode, where correlation between body part information and a cassette insertion order is registered as radiographing reservation information and a image is acquired, a third mode is available where image is acquired without registration of correlation as radiographing reservation information. These three modes are displayed to be selected and the process is continued thereafter according to the user's selected mode.

DETAILED DESCRIPTION OF THE PREFERRED EMBODIMENT

Preferred embodiments to achieve the aforementioned objective of this invention will be explained.

(1) The medical image creating system described in (A), wherein the first mode comprises at least a pre-registration mode or a post-registration mode.

(2) The medical image creating method described in (C), wherein the first mode comprises at least a pre-registration mode or a post-registration mode.

(3) The display controlling program described in (E), wherein the first mode comprises at least a pre-registration mode or a post-registration mode.

In order to achieve the aforementioned objective, another preferred embodiment will be explained.

As shown in a conventional technology, a conventional radiographic image diagnosis system is structured by targeting large hospitals where a plurality of radiographing apparatuses 4, readers 2 and controllers 3 are installed, a plurality of radiologists operate the radiographing apparatuses, and a plurality of doctors diagnose by using radiographic images acquired by radiographing apparatus 4. The images are acquired so as not to miscorrelate with each patient, by using a pre-registration mode, in which radiographing is conducted after correlation of body part information and a cassette as radiographing reservation information, or a post-registration mode, in which correlation of body part information and a cassette insertion order is registered as radiographing reservation information. However, it is rare that a doctor mistakes images in a small medical practitioner's clinic where there are fewer radiographing apparatuses 4, readers 2, controllers 3, radiologists and doctors, and patients. These smaller practices are accustomed to radiographing body parts in a predetermined manner, and therefore, it is desirable to conduct diagnosis by using a radiographic images as easily and quickly as possible.

This invention enables large hospitals and small clinics to acquire images according to one of the three modes. By establishing such a new convenient mode in which an image can be obtained without registering the correlation as radiographing reservation information, in addition to the pre-registration mode and the post-registration mode which are suitable for a large hospital, the Invention can be used in both large hospitals and the smaller medical practitioner's clinic.

Figure 1:
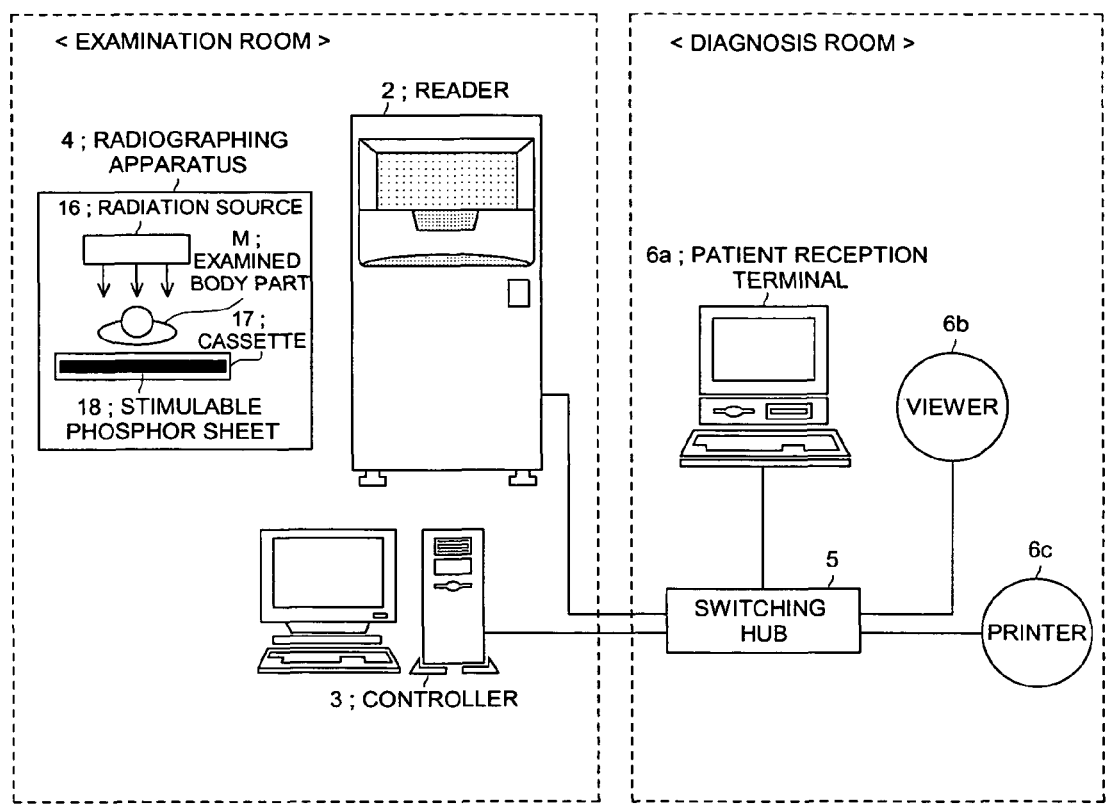
FIG. 1 is a diagram showing a structure of a radiographic image diagnosis system including a controller related to an embodiment of this invention.
Figure 2:
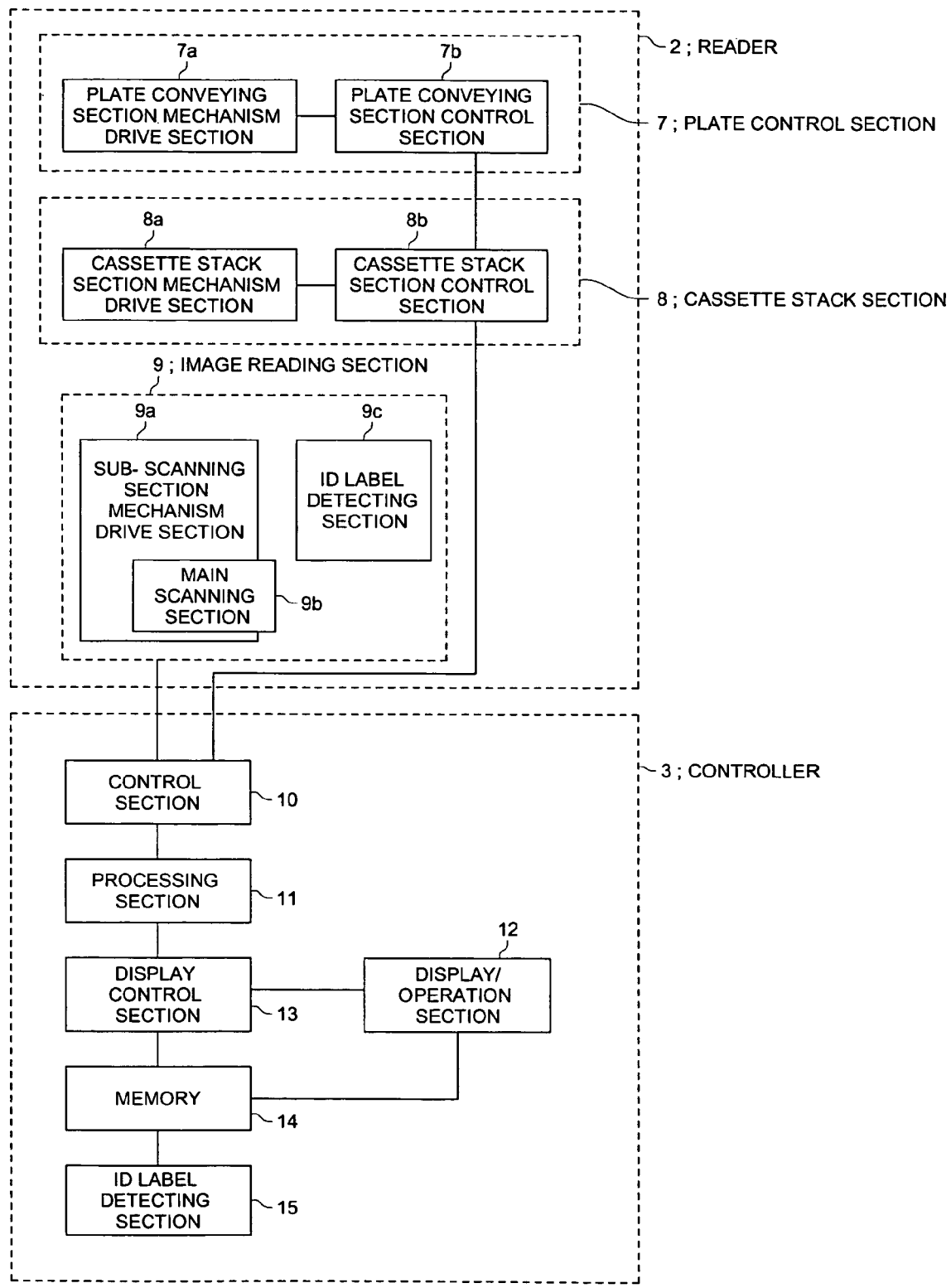
FIG. 2 is a block diagram showing a structure of a reader and a controller related to an embodiment of this invention.
Figure 3:
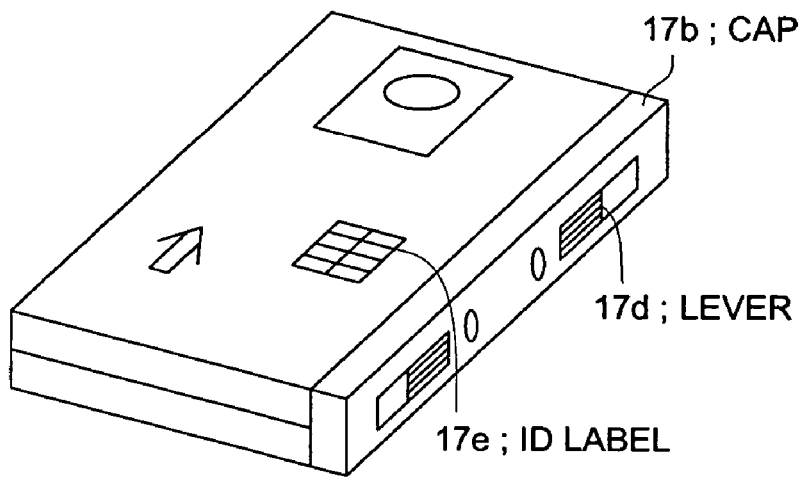
FIG. 3 is a perspective view showing a structure of a cassette used in a radiographic image diagnosis system related to an embodiment of this invention.
Figure 3:
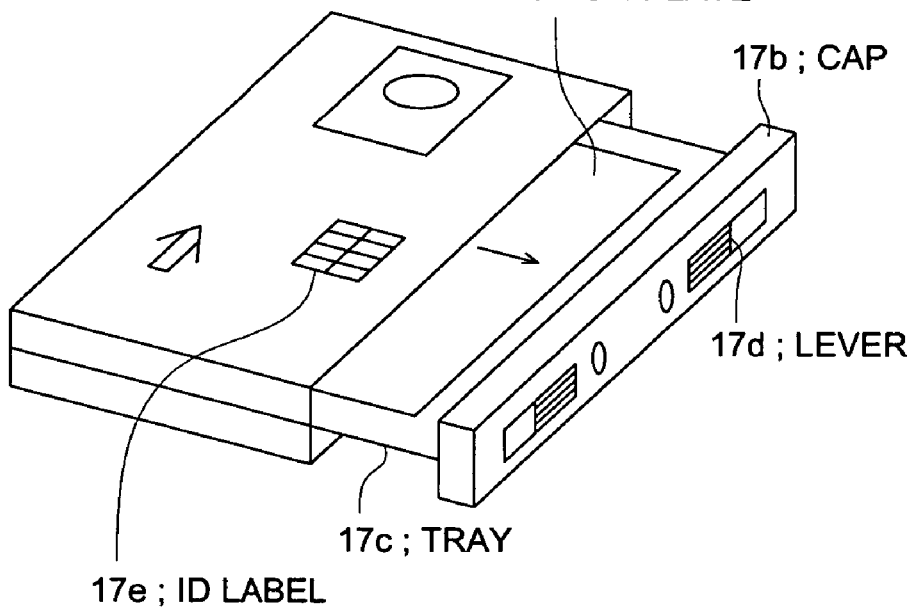
Figure 4:
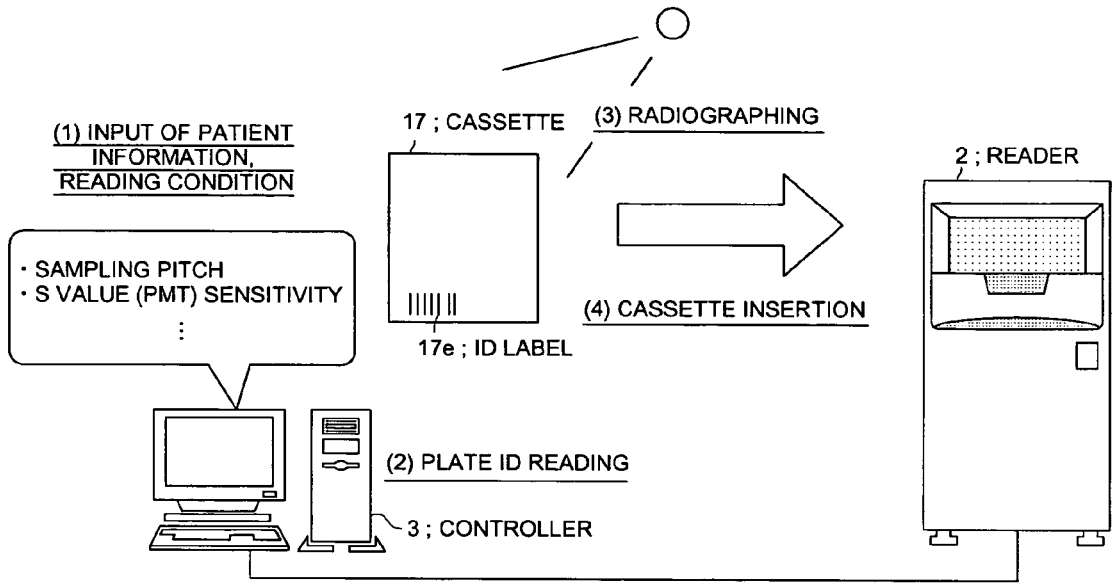
FIG. 4 is a schematic diagram showing a procedure of processing (pre-registration mode) in a radiographic image diagnosis system related to an embodiment of this invention.
Figure 5:
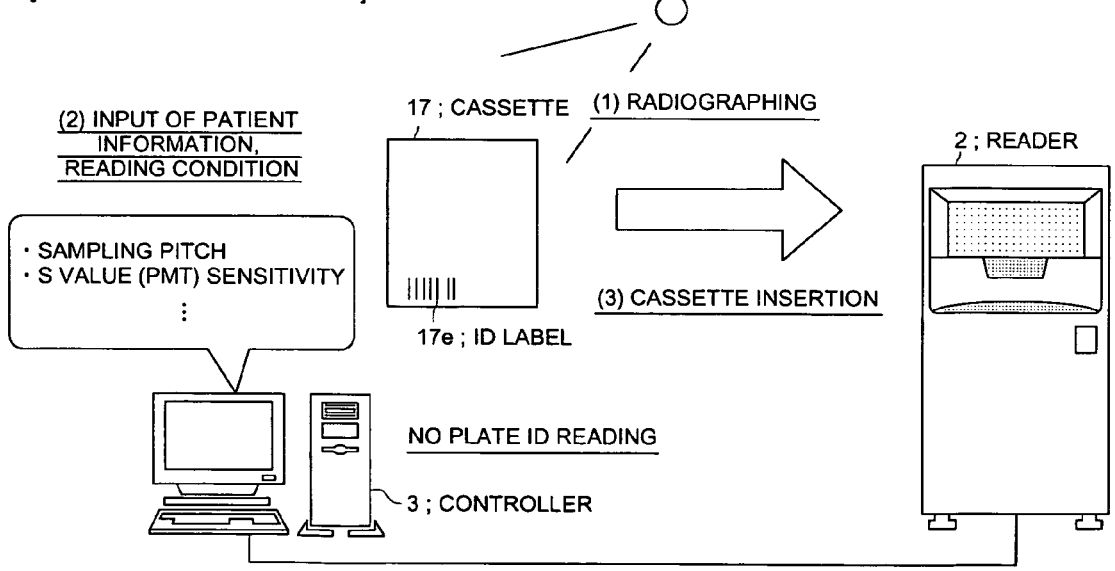
FIG. 5 is a schematic diagram showing a procedure of processing (post-registration mode) in a radiographic image diagnosis system related to an embodiment of this invention.
Figure 6:
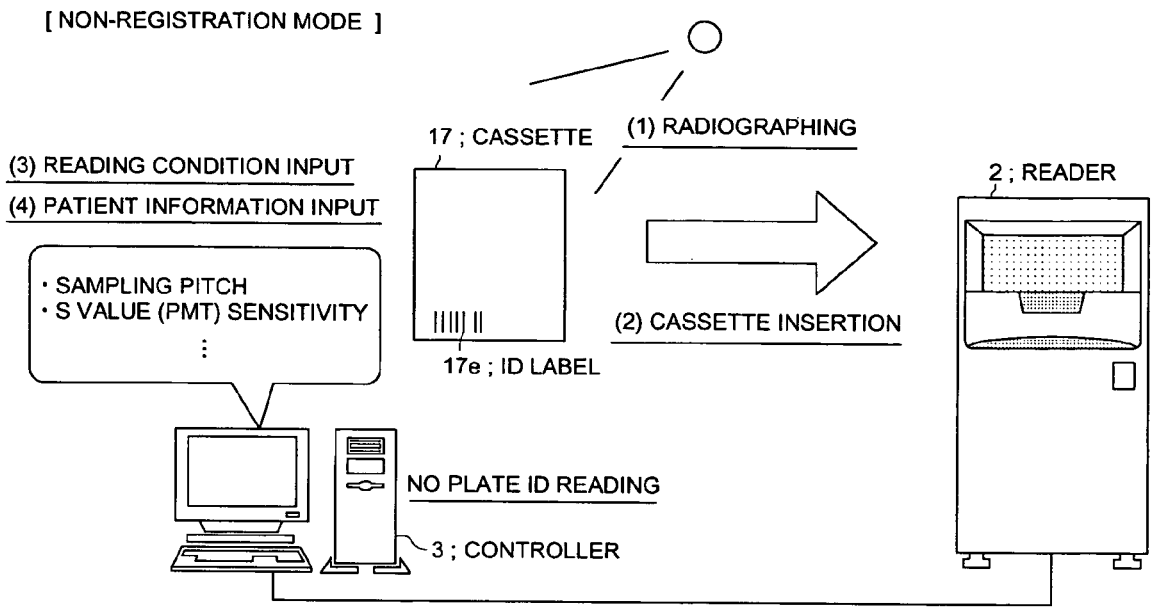
FIG. 6 is a schematic diagram showing a procedure of processing (non-registration mode) in a radiographic image diagnosis system related to an embodiment of this invention.

A medical image creating system, a medical image creating method and a display controlling program related to an embodiment of this invention will be explained referring to FIGS. 1 through 15 to explain the embodiment of the aforesaid invention in detail. FIG. 1 is a schematic diagram showing a structure of a radiographic image diagnosis system including a controlling apparatus (controller) of this invention. FIG. 2 is a block diagram showing a structure of an image reading apparatus (reader) and the controller. FIGS. 3(a) and 3(b) are perspective views showing the structure of a cassette. FIGS. 4 through 6 are diagrams explaining a registration system of radiographing conditions for image reading and FIGS. 7 through 14 are structural examples of images displayed by the controller. FIG. 15 is a flowchart showing a processing procedure employing the controller of this embodiment.

The following are only a few examples of applying this invention to radiographic image diagnosis system 1 of a cassette type, it is not limited to this embodiment and it can be applied to any apparatus displaying medical images, such as a system using other radiographic image transduction media and a system which directly takes out a radiographic image as digital signals by using a radiation detector such as an FPD. In this embodiment, reader 2 and controller 3 are arranged as separate means, however the controlling apparatus may be composed of their integration.

As shown in FIG. 1, in radiographic image diagnosis system 1, reader 2 reads out the radiographic image from cassette 17 where a latent image is formed by radiographing apparatus 4. Controlling apparatus (controller 3) displays the read image and/or inputs patient information and body part information as well as controlling the reading operation of reader 2 in an examination room where radiographing apparatus 4 is located. Reader 2 and controller 3 are connected to printer 6c, viewer 6b and patient reception terminal 6a which are installed according to the necessity via switching hub 5 as a LAN connection. Further, though it is not illustrated, these apparatuses are connected to other medical apparatuses by a network such as DICOM (Digital Image and Communications in Medicine). FIG. 1 is an example of radiographic image diagnosis system 1 and the number and/or the positioning of readers 2, controllers 3 and radiographing apparatuses 4 is not specifically limited.

Further, as shown in FIG. 2, reader 2, which reads image data acquired by radiographing apparatus 4. Controller 3, which controls the reading operation of reader 2, inputs patient information and/or body part information and displays a radiographic image based on image data. Reader 2 and controller 3 are directly connected or through a network. For example, reader 2 is composed of cassette stack section 8, which controls the insertion of cassette 17; plate controlling section 7, which controls the conveyance of a radiographic image transduction plate including stimulable phosphor sheet 18 drawn from cassette 17 (refer to FIG. 3 regarding a structure of cassette 17); and image reading section 9, which reads the latent image while scanning the radiographic image transduction plate.

In cassette stack section 8, cassette stack section mechanism drive section 8a and cassette stack section control section 8b are installed. Cassette 17 of a plurality of sizes can be set there. In plate control section 7, plate conveying section mechanism drive section 7a and plate conveying section control section 7b are installed. Plate conveying section control section 7b is controlled based on instructions from cassette stack section control section 8b. Plate conveying section mechanism drive section 7a draws a radiographic image transduction plate from cassette 17 and conveys it toward image reading section 9. In image reading section 9, sub-scanning section mechanism drive section 9a, main scanning section 9b and ID label detecting section 9c are installed. Main scanning section 9b is conveyed in the sub-scanning direction by sub-scanning section mechanism drive section 9a. Information of ID label (plate ID) attached to cassette 17 is read by ID label detecting section 9c while image reading is being conducted by laser scanning of main scanning section 9b.

Controller 3, which conducts the reading control of reader 2, inputs patient information and body part information and displays a radiographic image based on image data. It is equipped with control section 10 which controls reader 2, based on predetermined reading conditions. It is further equipped with processing section 11, which applies various image processing to an image read by reader 2 (such as contrast transformation processing, frequency processing, trimming, conversion/rotation and masking); display/operation section 12; display controlling section 13, which controls contents of display suitably for small scale users such as a medical practitioner's clinic; memory 14, which stores image data for display, radiographing condition parameters of each body part, image processing parameters for image processing for each specific body part optimally and each output format to output to a printer such as a laser imager; and ID label detecting section 15 reading plate ID of cassette 17. Each of the above-identified means can be structured in controller 3 as hardware and can also be structured as a display controlling program so that a computer can be structured to, at least, display controlling section 13, and the display controlling program is installed in controller 3 to perform.

This display controlling section 13, as will be described later, displays the three selectable modes, including a mode in which an image is acquired without registration of radiographing reservation information for correlating (hereinafter referred to as non-registration mode), as well as the pre-registration mode, in which radiographing is carried out after registration of correlation between body part information and a cassette as radiographing reservation information on an optional screen such as the initial screen, and the post-registration mode, in which registration of correlation between body part information and a cassette inserting order is carried out as radiographing reservation information.

Radiographing condition parameters stored in memory 14 are parameter set corresponding to each body part to be radiographed, reading conditions in the image reading stage of reader 2 (such as sampling pitch and sensitivity of reading), and the ID number of image processing parameters.

These image processing parameters are parameters which applies for optimal image processing to a certain body part, and stores parameter values of each image processing, such as a look-up-table defining the gradation curve of contrast transformation processing and the accentuation level of frequency processing sorted for each specific body part. The output format is a format which defines how many images of image data is stored, in which direction each image of image data is oriented on a single film when an image is outputted to printer 6c, such as a laser imager, and one or plural images of image data is incorporated into an output format which the operator selected on display, operating section 1 and each image of image data and additional information such as format information are outputted to DICOM printer 6c.

In the above cassette type radiographic image diagnosis system 1, image data are read after employing one of among the pre-registration mode and the post-registration mode, which are convenient to use for large hospitals having a plurality of radiographing apparatuses 4, readers 2, controllers 3 and radiologists, and non-registration mode, which is convenient for a medical practitioner's clinic having a fewer radiographing apparatuses 4, readers 2, controllers 3 and radiologists.

Regarding input of body part information, a choice of a normal mode and a repeat mode are provided. In the normal mode, whenever body part information is inputted on display/operation section 12 of controller 3, radiographing of the body part is reserved. On the other hand, in the repeat mode, the selected body part information is preserved as a setting value of body part information for the reading operation, and after this, input of body part information can be omitted and the repetition image reading is of the same body part.

Operations of the pre-registration mode, the post-registration mode and the non-registration mode of the normal mode will be explained via FIGS. 4 through 6.

In the case of the pre-registration mode, as shown in FIG. 4, an operator such as radiologist inputs patient information and body part information on display/operation section 12 ((1) in FIG. 4). At this time, information of ID label 17e (refer to FIGS. 3(a) and 3(b)), which has been attached on cassette 17, is read by ID label detecting section 15 of controller 3 ((2) in FIG. 4). Then, inputted body part information and plate ID are correlated and stored. After this, radiographing is performed by using the registered cassette 17 ((3) in FIG. 4), and cassette 17, where latent image has been formed, is inserted into reader 2 ((4) in FIG. 4). In reader 2, plate ID of cassette 17 is read by built-in ID label detecting section 9c, and body part information corresponding to this plate ID is searched for and acquired. Further, a parameter set of radiographing conditions corresponding to the body part information, and reading conditions for reading an image by reader 2 are acquired. Then, reading of an image is conducted according to the acquired reading conditions. The read image data is sent to the controller. In the controller, the ID number is acquired from a radiographing condition parameter set and image processing is applied to the read image according to the image processing conditions based on the image processing parameters.

In the case of the post-registration mode, as shown in FIG. 5, an operator such as a radiologist first performs X-ray radiographing ((1) in FIG. 5), and after this, patient information and body part information is inputted on display/operation section 12 of controller 3 ((2) in FIG. 5). Here, in this case, correlation between the plate ID and body part information is not carried out. Instead, the operator correlates the inputted body part information and the insertion order of cassette 17 into reader 2, and correlates and stores inputted body part information and the insertion order. When cassette 17, on which a latent image has been formed, is inserted into reader 2 ((3) in FIG. 5), reader 2 searches for and acquires body part information corresponding to the insertion order and further reads out the radiographing condition parameter set corresponding to the body part information. It then acquires reading conditions from the parameter set to perform a reading operation of an image according to the reading conditions. After this, as in the pre-registration mode, the read image data are sent to the controller 3, which acquires the ID number of the image processing parameters from the radiographing condition parameter set in order to perform image processing to the read image according to the image processing conditions based on the image processing parameters.

In the case of the non-registration mode, as shown in FIG. 6, an operator such as radiologist first performs radiographing ((1) in FIG. 6), and after this, cassette 17, where a latent image has been formed, is inserted into reader 2 ((2) in FIG. 6). When the operator inputs body part information on display/operation section 12 of controller 3 ((3) in FIG. 6), reader 2 reads out the radiographing condition parameter set and acquires reading conditions from the parameter set in order to perform a reading operation according to the reading conditions. Then, the read image data are sent to the controller 3, where the controller acquires the ID number of the image processing parameters from the radiographing condition parameter set in order to perform image processing of the read image according to the image processing conditions based on the image processing parameter. After displaying the image, input, such as input of patient information, is conducted ((4) in FIG. 6).

In the following paragraphs, the repeat mode of the pre-registration mode, the post-registration mode and the non-registration mode will be explained.

In the case of the pre-registration mode, first an operator selects body part information on display/operation section 12 of controller 3. Whenever plate ID is read, the selected body part information and the plate ID are correlated and stored as radiographing reservation information. The operation hereafter is the same as in the normal mode of the pre-registration mode.

In the case of the post-registration mode, first the operator selects body part information on display/operation section 12 of controller 3. Whenever cassette 17 is inserted into reader 2, radiographing condition parameters of the selected body part are read out, and the image is read by acquiring reading conditions from the parameter set. Thereafter, the read data are sent to the controller, where the ID number of the image processing parameters is acquired from the radiographing condition parameters in order to apply image processing to the read image, according to image processing conditions based on the image processing parameter.

In the case of non-registration mode, as in the post registration mode, the operator selects body part information on display/operation section 12 of controller 3. After this, whenever cassette 17 is inserted into reader 2, radiographing condition parameters of the selected body part information are read out and an image is acquired reading conditions from the parameter set. Thereafter, the read data are sent to controller 3 where the ID number of image processing parameter is acquired from radiographing condition parameter set in order to apply image processing to the read image, according to image processing conditions based on the image processing parameter.

Each of the pre-registration mode, the post-registration mode and the non-registration mode has an advantageous feature. For example, in a hospital where many readers 2 and controllers 3 are installed in various places and a plurality of radiologist perform radiographing, radiographic image diagnosis to a plurality of patients can be conducted accurately by using the pre-registration mode or the post-registration mode. In a smaller medical practitioner's clinic where, for example, one reader 2 and one controller 3 are installed and one doctor works as the above-mentioned radiologist, the radiographing is conducted quickly and effectively by using the non-registration mode. Setting of the pre-registration mode, the post-registration mode and the non-registration mode and setting of the normal mode and the repeat mode can be chosen on the mode selection screen, which will be described later, and unless the setting is changed, the previous setting is maintained.

Next, a procedure to output a radiographic image of a patient, by means of radiographic image diagnosis system 1 of the abovementioned structure, on a printer such as a laser imager or a host terminal for the patient reception after radiographing will be explained referring to examples of screen structures in FIGS. 7 through 14 and the flowchart in FIG. 15.

The normal mode procedure will be explained below, however, the operation of the repeat mode after the step of reading image data is identical.

Figure 7:
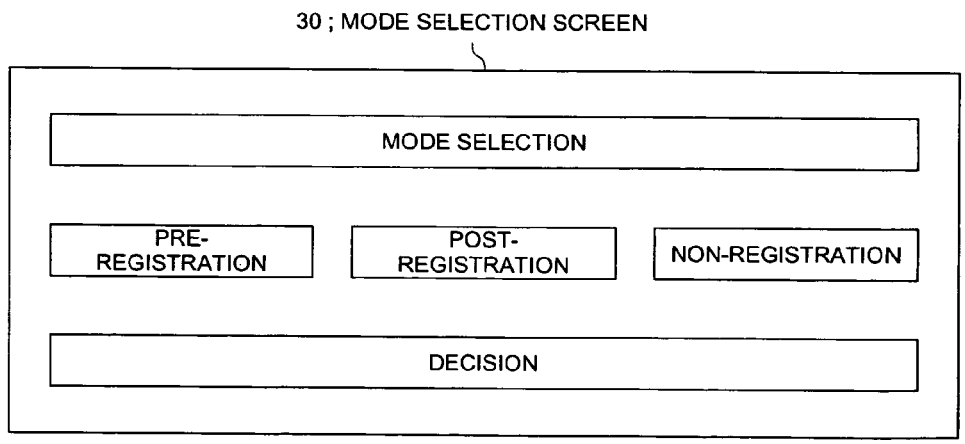
FIG. 7 is a diagram showing a structural example of a screen (mode selection screen) displayed on the display section of a controller related to an embodiment of this invention.

First, in Step S101, mode selection screen 30, shown in FIG. 7, is displayed on display/operation section 12 of controller 3 as an initial screen. Mode selection screen 30 is displayed so that three registration modes of the pre-registration mode, the post-registration mode and the non-registration mode are displayed for selection. In Step S102, after an operator touches the mode selection button to select the desired mode among the three, an image is acquired according to the selected mode. The three registration modes of the pre-registration mode, the post-registration mode and the non-registration mode will now be explained.

[Pre-Registration Mode]

Figure 8:
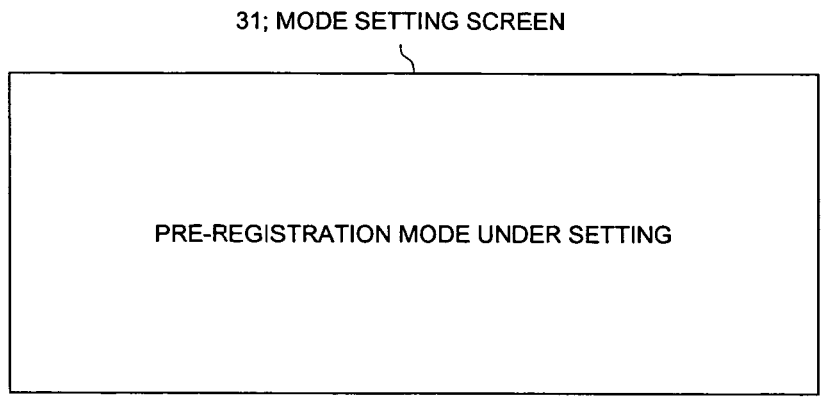
FIG. 8 is a diagram showing a structural example of a screen (mode setting screen) displayed on the display section of a controller related to an embodiment of this invention.
Figure 8:
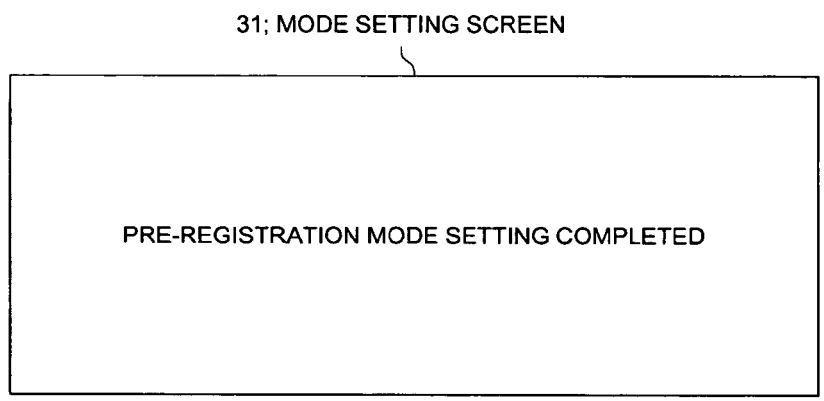

For example, when the pre-registration mode is selected in Step S102, after mode setting screen 31 shown in FIG. 8 (a) and FIG. 8(b) is displayed on display/operation section 12 of controller 3, the patient information input screen (not illustrated) is displayed on display/operation section 12 of controller 3. When information of a patient to be examined is inputted in Step S103, body part selection screen (not illustrated) is displayed on display/operation section 12 of controller 3.

Next, after an operator inputs body part information by using the patient information input screen in Step S104, information of ID label 17e attached to cassette 17 is read out by ID label detecting section 15 of controller 3 and stored after correlating the ID label information (plate ID) with the body part information in Step S105.

Next, in Step S106, by means of a commonly known method, a patient is radiographed by using radiographing apparatus 4, such as an X-ray radiographing apparatus. An X-ray transmission image of the patient is recorded on the radiographic image transduction plate, in cassette 17, as a latent image. Here, radiographing is not limited to only radiographing apparatus 4, but may also include apparatus which images patient by magnetism or by ultra-sound waves or any imaging apparatus used in the medical field.

Next, an operator, such as a radiologist, removes cassette 17 from radiographing apparatus 4 and inserts it into any one of the slots of reader 2 in Step S107. Reader 2 reads the plate ID by ID label detecting section 9c and searches the database for stored radiographing reservation information, while using the plate ID as a searching key to pick up body part information corresponding to the plate ID. After this, in Step S108, reader 2 reads out radiographing condition parameters correlated with the body part information, picks up the reading conditions out of them and reads the latent image on the radiographic image transduction plate according to the reading conditions.

As a reading procedure, first, according to the value of reading sensitivity, the sensitivity of image reading section 9 is set. According to the value of reading resolution, the conveyance speed of plate conveying section mechanism drive section 7a, and the sampling pitch of A/D converter installed in image reading section 9, are also set. Radiographic image transduction plate is removed from cassette 17, and image data stored and preserved on the radiographic image transduction plate is read out, while the radiographic image transduction plate is sub-scanned in the X direction by sub-scanning mechanism drive section 9a.

When excitation light exposes the radiographic image transduction plate, energy stored in the phosphor is stimulated and converted into electric signals by image reading section 9. These electric signals are applied with logarithmic transformation by a logarithmic converter, whereby electric signals starting with a proportional relationship with light intensity are converted into electric signals displaying a logarithmic linear relationship with the intensity of the stimulation light. That is, electric signals have a linear relationship with the density, and are further digitized by A/D converter.

The digitized image data outputted from the aforementioned image reading section 9 is displayed on an image display screen (not illustrated) at any time during the reading step.

After this, radiographing condition parameters corresponding to body part information is read out and the stored image processing parameter ID number is acquired. Next, the image processing parameter set specified by the ID number is read out, and image processing conditions are determined based on the image processing parameters. At this time, the ID number of the image processing parameter corresponding to each image is stored in the memory for every image. According to the determined image processing conditions, read image data are applied for image processing, such as contrast transformation processing and frequency processing (Step S109). After completion of the image processing, the image data before image processing, which were displayed on the image display screen in the aforementioned reading step, are replaced by image data after image processing (Step S110).

[Post-Registration Mode]

In Step S102, when the post-registration mode is selected, the mode selection screen 31 is displayed on display/operation section 12 of controller 3 and the post-registration mode is set. In the post-registration mode, in Step S111, by means of a known method, a patient is radiographed by using radiographing apparatus 4, such as an X-ray radiographing apparatus. The transmitted X-ray image of the patient is recorded as a latent image on the radiographic image transduction plate in cassette 17.

Next, when the information of the patient to be examined is inputted in Step S112, by using the patient information input screen (not illustrated) displayed on display/operation section 12 of controller 3, the body part selection screen (not illustrated) is displayed on display/operation section 12 of controller 3, and the operator inputs body part information by using the patient information input screen in Step S113.

Next, an operator, such as a radiologist, removes cassette 17 from radiographing apparatus 4 and inserts cassette 17 into any one of the slot of reader 2 in Step S114. The cassette insertion order queue and body part reservation queue are correlated, and information corresponding to the insertion order is selected, based on the correlation. Next, in Step S116, reader 2 reads out radiographing condition parameter correlated with body part information, picks up reading conditions out of them, and reads the latent image on the radiographic image transduction plate, according to the reading conditions.

After this, radiographing condition parameters corresponding to the body part information is read out, and the image processing parameter ID number stored in it is acquired. Next, the image processing parameter set specified by the ID number is read out, and the image processing conditions are determined based on the image processing parameters. At this time, the ID number of the image processing parameter corresponding to each image is stored in the memory for every image. According to the determined image processing conditions, the read image data is applied with image processing such as contrast transformation processing and frequency processing (Step S117). After completion of the image processing, image data before the image processing, which were displayed on the image display screen in the aforementioned reading step, are replaced by image data after the image processing (Step S118).

[Non-Registration Mode]

In Step S102, when the non-registration mode is selected, the mode selection screen 31 is displayed on display/operation section 12 of controller 3, setting the non-registration mode. In the non-registration mode, a patient is first radiographed by using radiographing apparatus 4, such as radiographing apparatus in Step S119. Then the transmitted X-ray image of the patient is recorded as a latent image on a radiographic image transduction plate in cassette 17 as in the post-registration mode.

In the post-registration mode, patient information and/or body part information are eventually inputted. However, in the case of small medical practitioner's clinic, the correlation is not necessary because the number of patients or radiographing taken at a time is not large enough so as to mistake the images. Therefore, in the non-registration mode, cassette 17 is taken out of radiographing apparatus 4 without inputting patient information and/or body part information, and cassette 17 is inserted into any one of the slots of reader 2 in Step S120.

Figure 11:
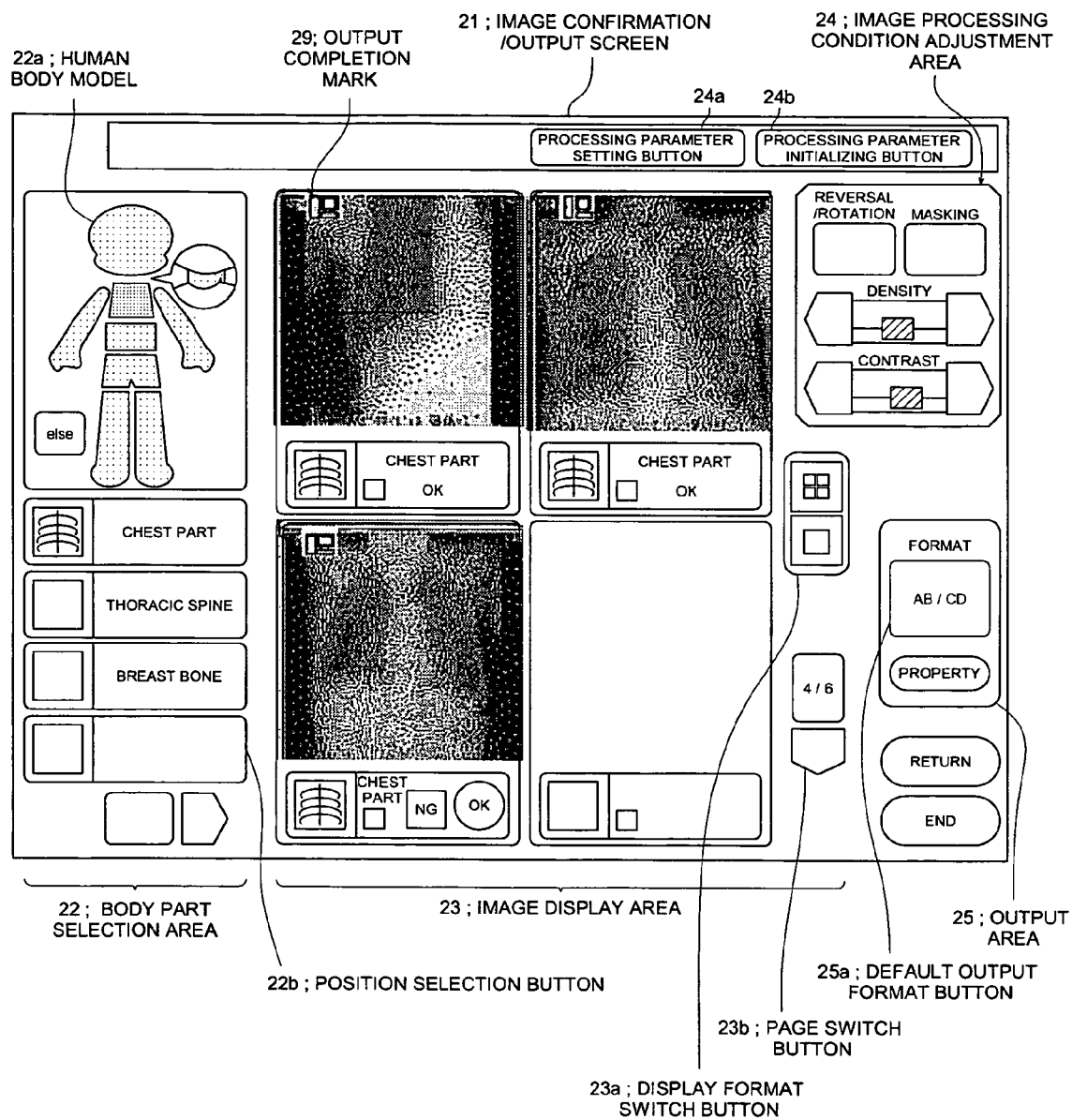
FIG. 11 is a diagram showing a structural example of a screen (image confirmation/output screen) displayed on the display section of a controller related to an embodiment of this invention.

Next, in Step S121, body part information is inputted. However, for ease of use by a medical practitioner's clinic employing the non-registration mode, it is structured so that body part information is inputted by means of image confirmation/output screen 21 as shown in FIG. 11. On this image confirmation/output screen 21, because body part or radiographing direction is limited for a small scale user, such as a medical practitioner, there are provided on body part selection area 22, the first selection area including a schematic diagram of a human body (human body model 22a). Any predetermined area (for example, the head, cervical part, chest, abdomen, pelvis, extremities and other body part) is selectable. A second selection area, including body part selection button 22b, where body parts included in the selected area of human body model 22a (for example, in the case of the head area: head survey, cheek bone, jaw, nasal bone, acoustic organ and jaw; in the case of the cervical area: cervical vertebra, pharynx and larynx; in the case of chest area: chest, thoracic spine and breast bone; in the case of the abdomen area: abdomen, thoracic lumbar vertebrae, lumbar vertebrae and ribs; in the case of pelvis area: pelvis and hip joint; in the case of the extremities: Achilles tendon, axial heel, sesamoid bone; in the case of other body views: abdomen KUB/DIP, DIC/bladder contrast, neonatal chest abdomen, neonatal bones, cephalo, pantomography, parotid gland, submandibular gland, entire spine, long lower extremities) are displayed and are selectable, thereby allowing easy selection of the desired body part.

More specifically, when an operator selects a specific part of human body model 22a (for example, chest part), a detailed part in the area of the selected part (such as chest part, thoracic spine, breast bone) is displayed on body part selection button 22b, as a list of selectable body parts. The operator obtains body part information by selecting a detailed body part from among them.

Next, in Step S122, radiographing condition parameters correlated with body parts information is read out in reader 2, and further, reading conditions are picked up to read the latent image on the radiographic image transduction plate according to the reading conditions.

After this, as in the pre-registration mode and the post-registration mode, radiographing condition parameter corresponding to the body part information is read out, and the stored ID number of image processing parameters is acquired. Next, the image processing parameter set, specified by the ID number, is read out whereby image processing conditions are determined based on the image processing parameters. At this time, the ID number of the image processing parameters corresponding to each image is stored in the memory for every image. According to the determined image processing conditions, the read image data is applied for image processing, such as contrast transformation processing and frequency processing (Step S123). After completion of image processing, image data before the image processing, which were displayed on the image display area 23 of image confirmation/output screen 21 in the reading step, are replaced by image data after the image processing (Step S124). After the image is displayed, patient information is inputted by using the patient information input screen (not illustrated) in Step S125.

Figure 9:
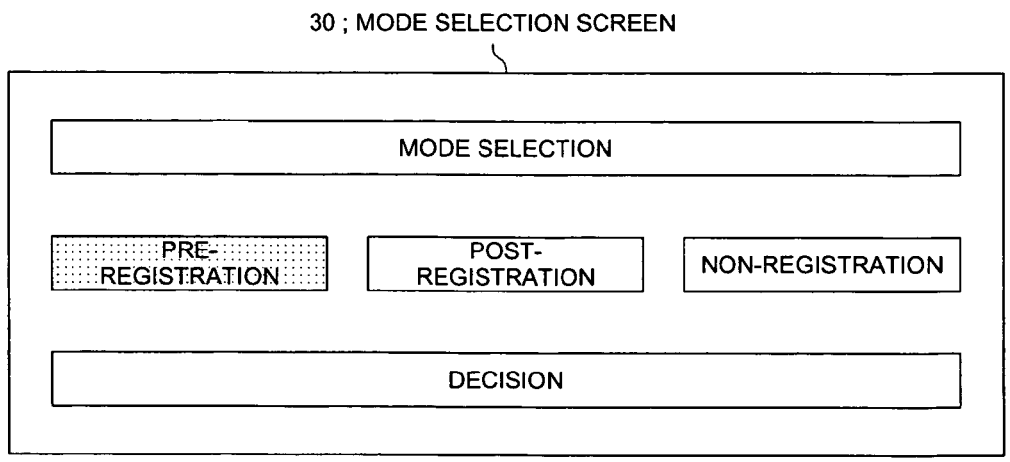
FIG. 9 is a diagram showing a structural example of a screen (mode selection screen) displayed on the display section of a controller related to an embodiment of this invention.
Figure 10:
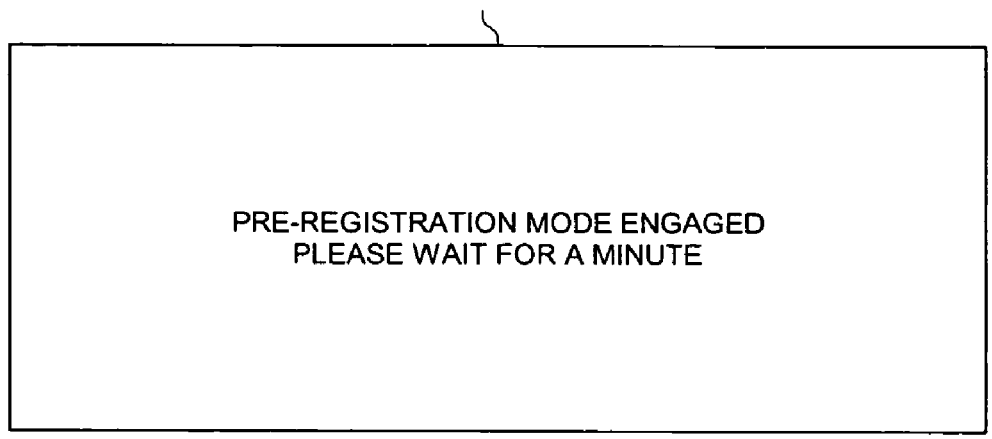
FIG. 10 is a diagram showing a structural example of a screen (mode setting screen) displayed on the display section of a controller related to an embodiment of this invention.

In the above explanation, mode selection is conducted by means of mode selection screen 30 at the initial stage. However, the mode can be changed at any moment (but normally after completion of the examination) by returning to mode selection screen 30. For example, when processing is performed in the pre-registration mode as shown in FIG. 9, mode selection screen 30 is displayed to recognize the presently set mode, by pushing a button previously provided on the image display screen. When another mode is selected on mode selection screen 30, if the present set mode is not used, the screen shown in FIG. 8 is displayed and the setting is changed to the new mode. If the present set mode is in use by other users, mode setting screen 31 shown in FIG. 10 is displayed to notify impossibility to the operator.

As shown above, the desired mode can be selected from among the pre-registration mode, the post-registration mode and the non-registration mode. Because subsequent processing is conducted according to the selected mode, an image is obtained by an optimal procedure.

After using any of the above-mentioned mode, it is possible to adjust the image process conditions to output an image. The processing conducted by using the abovementioned image confirmation/output screen 21 will now be explained. For example, when the image displayed on image display areas 23 is not the desired image by the operator, slight adjustments of image processing conditions on image processing condition adjustment area 24 (Step S126) can be performed. Previously, it was necessary to select the screen for the image processing condition adjustment and to adjust the conditions of image processing on this image processing condition adjustment screen, when the image processing condition for the displayed image was to be adjusted. However, density or contrast of the image can now be adjusted by a button or a slide bar without changing the screens, by providing image processing condition adjustment area 23 of image confirmation/output screen 21. Here, tone processing is picked up and an example of the parameter change of density (maximum density) and contrast (.gamma. curve) is shown as an example of adjustable image processing. Adjustment of parameter related to other processing such as accentuation level in frequency processing may also be adjustable. Further, in FIG. 11, although image processing condition adjustment area 24 is provided in the upper right of image confirmation/output screen 21, the structure or the position of image processing condition adjustment area 24 is optional, and a layout change of each area, such as a change of the position of image processing condition adjustment area 24 and body part selection area 22, can be carried out according to the use conditions after the image is displayed on image display area 23.

As mentioned above, because image data, which are processed according to the image process conditions after adjustment, are immediately displayed on image display area 23, the operator can obtain the desired image by repeating the adjustment operation on image processing condition adjustment area 24 while confirming the image (Step S127).

It is possible that the simultaneous adjustment of these image processing conditions can be carried out to a plurality of images. In this case, a plurality of images are set in a selected condition and the same variation amount is added to all the image processing conditions of all the images set in the selected condition, by an adjusting operation on the image processing condition adjustment section, and images which are image-processed by the new image processing conditions are subsequently displayed on image display area 23. In the condition where an image is selected, if the processing parameter setting button is pushed, the image processing parameter is renewed (overwritten) by that which was used when the selected image was image-processed.

More specifically, because image processing conditions used in the last image processing for each image are stored in the memory, when processing parameter setting button 24*a* is pushed, the image processing conditions stored in memory 14 are read out, and image processing parameter values which are likely to determine the image processing conditions are calculated reversely, based on the image processing conditions. Next, the ID number of the image processing parameters referred to during the image processing of the image is acquired from the memory. Then the image processing parameter values, calculated reversely from the image processing condition, overwrite the stored image processing parameters having the ID number.

In the condition where any one image is selected, when processing parameter initializing button 24*b* is pushed, the image processing parameters which were referred during the image processing of the selected image, are changed to the initial setting prior to the manufacturer's shipment. Specifically, regarding each image processing parameter set corresponding to each body part, the parameter values of the manufacturer's initial setting and the parameter values referred to during the image processing are both stored in memory 14. At shipment from the manufacturer, the parameter values of manufacturer's initial setting are set as the parameter values to be referred to during image processing. When the processing parameter initializing button 25*b* is pushed, the ID number which was referred to during the image processing of the image is acquired from memory. The parameter values of manufacturer's initial setting are read out from the memory means and the parameter values of manufacturer's initial setting overwrite the parameter value referred to during the image processing which is stored in memory 14.

Further, in addition to providing a processing parameter undo button, it can be structured so that the latest image processing parameter values before it is changed are stored in memory 14 for every image processing parameter corresponding to each body part. Then when processing parameter setting button 24*a* is pushed, image processing parameter values before the change are stored, and when the processing parameter undo button is pushed, image processing parameters referred to during image processing may overwrite the image processing parameter values before the change.

Default output format button 25*a* in output area 25 is used to select the output format when data are outputted to a printer such as a laser imager. Every time when default output format button 25*a* is pushed, the default format to be outputted is arranged to be changed to the next one of some prescribed formats one after another in the order, and therefore, one of formats is always stored in the selected condition and the selected format name is displayed on the button.

Specifically, in this example, as patterns to arrange and output a plurality of images on one sheet of film, there are provided six patterns of "A", "AA", "A/A", "AB", "A/B", "AB/CD". "A" represents a format for outputting one image, "AA" represents a format for outputting two images so that two images are created by applying two different image processing to one image, which are arranged side by side, "A/A" represents a format for outputting two images so that the two images created by applying two different image processing to one image are arranged up and down to output. "A/B" represents a format outputting two different images arranged up and down to output. "AB/CD" represents a format outputting four images so that four different images are arranged in two vertical rows and in two horizontal rows. Accordingly, each of formats "A", "AA", "A/A" needs image data for one image, each of formats "AB", "A/B" needs image data for two images and format "AB/CD" needs image data for four images.

The size and direction of film to be outputted can be set on the output property screen, which will be described later. If all the image data of the format designated with default output format button 25*a* can not be included in a film of the set size, the area size which is acquired when the film is equally divided by the number of images of image data to be outputted according to this format, is calculated to be the image size to be cut-out for one image of image data. At this time, on each image of the image data displayed in image display area 23, the image size to be cut-out for each image is displayed as frame lines when image data are outputted according to this default output format. In the default output format, the image of image data are cut-out so that the distances to the upper and lower edges from the cutout position are the same as well as the distances to left and right edges from the cutout position are also the same. This cutout position is changeable on the output property screen, which will be described later.

In screen display area 23, an OK button and a NG button are provided, and an operator confirms the screen displayed in image display area 23 in Step S128, and then when a desired image is obtained, pushes the OK button, and if the acquired one is not the desired one, the NG button is pushed. When the NG button is pushed, the display of the image data is deleted in image display area 23 and the image data is also deleted in memory 14.

When the OK button is pushed, an OK mark is added near the image data showing that the image data were confirmed, and then the OK button and the NG button, which have been displayed, are deleted. The image data for which the OK button was pushed are incorporated in the default output format queue. If the number of images of image data stored in the default output format queue accords with the number of images of image data the format of which was designated by the default output format button, print preview screen 26, which shows the film output image of the format shown in FIG. 12, is displayed.

Figure 12:
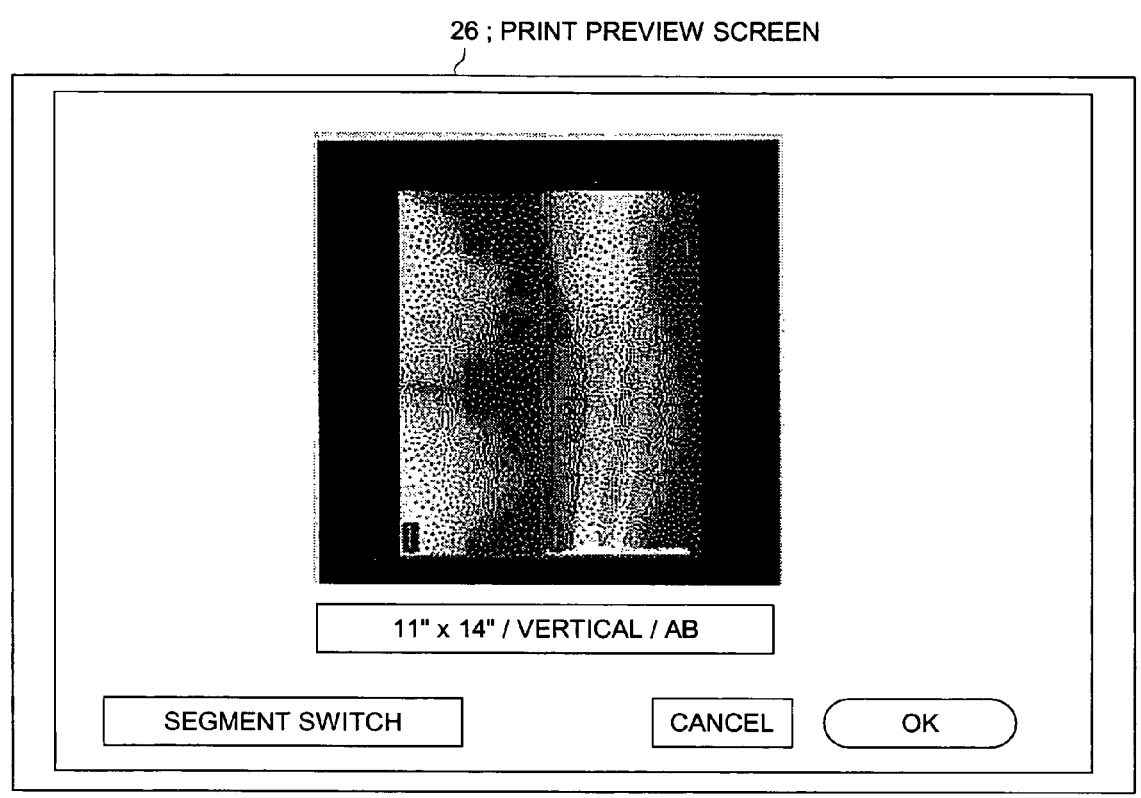
FIG. 12 is a diagram showing a structural example of a screen (print preview screen) displayed on the display section of a controller related to an embodiment of this invention.

In print review screen 26, when the OK button is pushed, displayed image data of output image is outputted to a printer such as a laser imager, and print preview screen 26 shown in FIG. 12 is closed. Then, image data outputted to a printer are taken out of the default output format queue. In the case where the cancel button is pushed on print review screen 26, only print preview screen 26 is closed, without any output to a printer. At this time, the image data for which the OK button was pushed most recently on image display area 23 of image confirmation/output screen 21 is taken out of the default output format queue.

When property button in area 25 is pushed on image confirmation/output screen 21, the output property screen is displayed. On this screen, an operator selects the destination for output with the output destination selection button.

Figure 13:
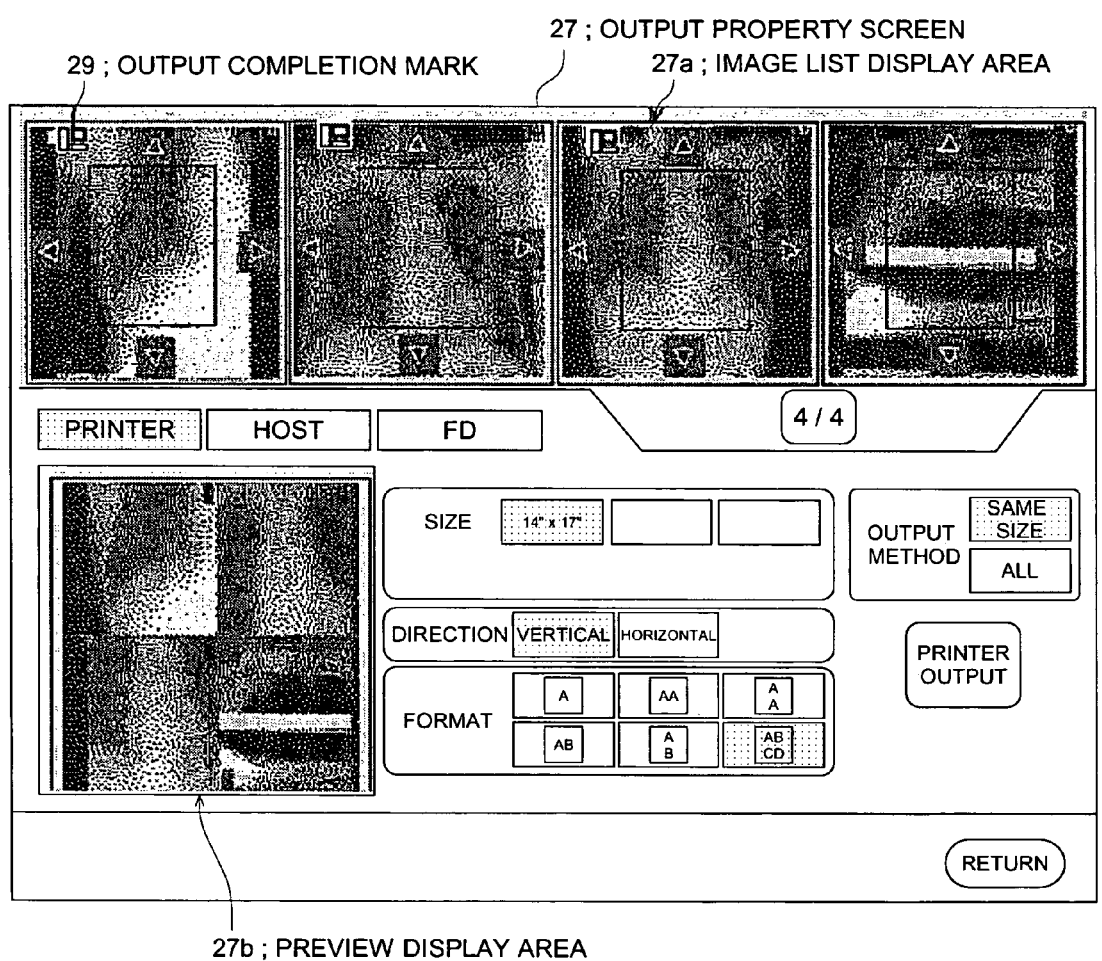
FIG. 13 is a diagram showing a structural example of a screen (output property screen) displayed on the display section of a controller related to an embodiment of this invention.

FIG. 13 is an example of the structure of output property screen 27 when a printer is selected as an output destination. An operator selects the film size with the size selection button and then instructs which direction, vertical or horizontal, the film is placed with the film direction selection button. Next, the output format is selected with the format selection button (Step S129). The position of an image of image data in one film is displayed on preview display section 27b. This display is separated by divisions of area size corresponding to image data of one image.

On the upper end of the screen is image list display section 27a where image data which has been read are displayed. When one image is selected from this image list display section 27a, and then a division of image data is selected on preview display section 27b, image data are allocated in the position of the selected division of the format.

It is possible to change the cutout size when image data is arranged to the format with the cutout size selection button. When the "all" button is pushed, each image of image data to be located in the output format is reduced to the area size corresponding to the divisions in the output format to display the entire image. When the "same size" button is selected, the scale is not changed and data of the corresponding area size in the output format is cutout from the image data.

In image list display section 27a, cutout size/position is displayed with frame lines for each image when it is outputted according to the selected output format, and the cut-out position is adjusted by adjusting these frame lines with an operation of the cutout position adjusting button. At this time, if the image to be applied with adjustment of the cutout position has been located in a division of the output format displayed on preview display section 27b, the image of the image data cut out at the cutout position is displayed on preview display section 27b, being linked with the adjustment of the cutout position on image list display section 27a. When the output button is pushed, the image data are outputted to a printer such as a laser imager according to the format and the image position is displayed on preview display section 27b.

Figure 14:
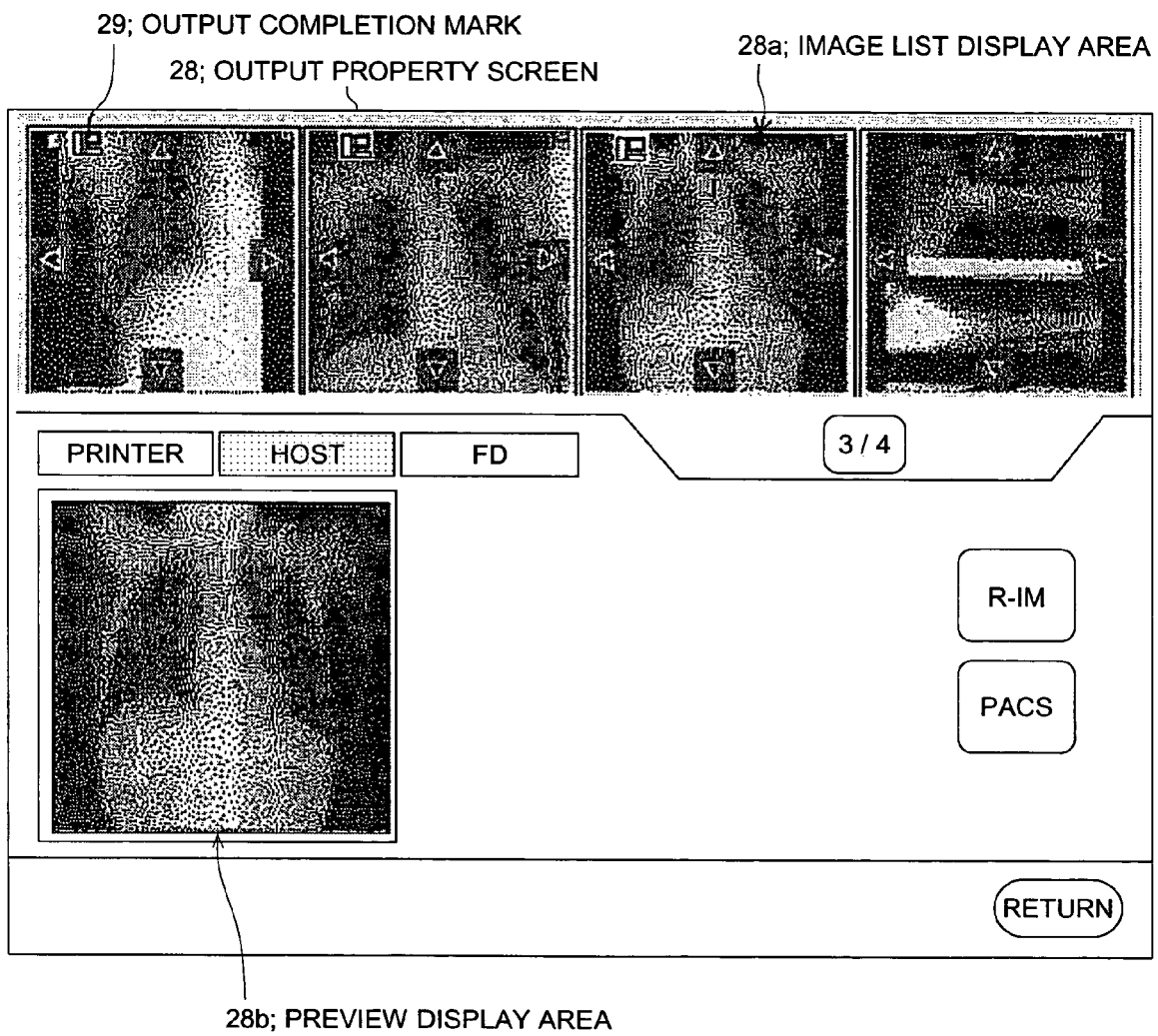
FIG. 14 is a diagram showing a structural example of a screen (output property screen) displayed on the display section of a controller related to an embodiment of this invention.
Figure 15:
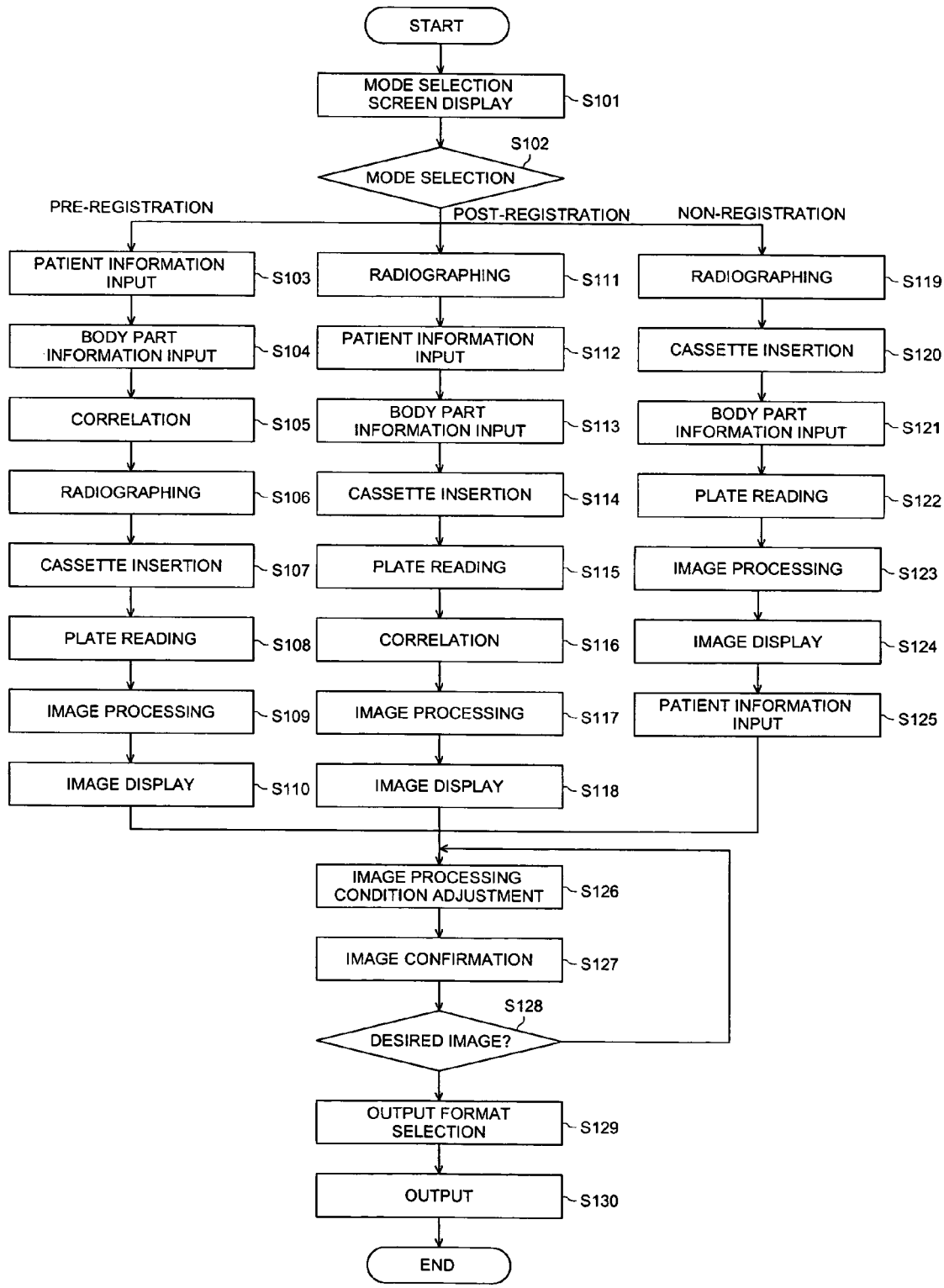
FIG. 15 is a flowchart showing a series of processing employing a controller related to an embodiment of this invention.
Figure 16:
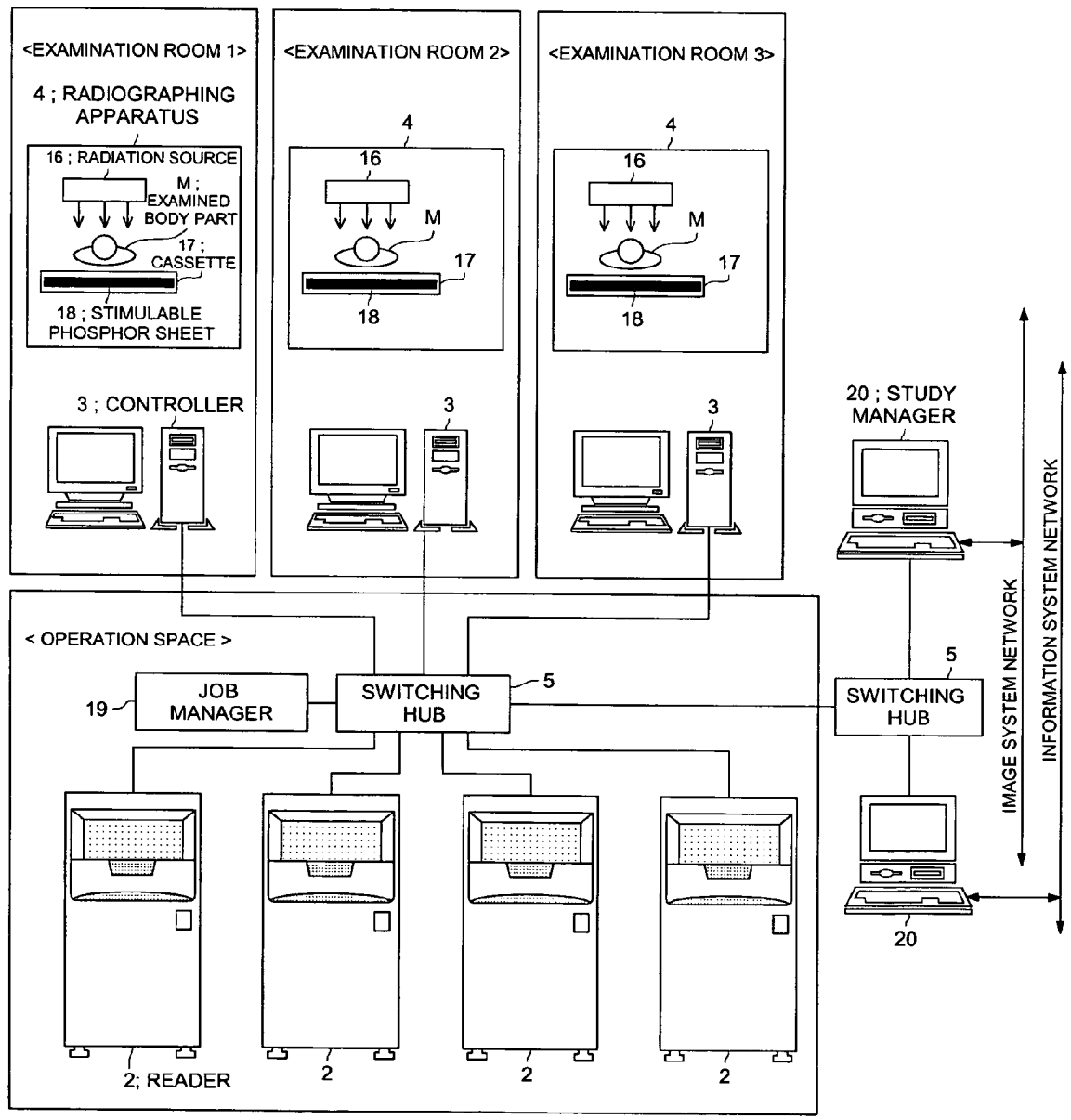
FIG. 16 is a schematic diagram showing a structure of a conventional radiographic image diagnosis system.

FIG. 14 is an example of a structure of output property screen 28 in the case of selecting the host as an output destination. The operator selects an image from image list display section 28a in the upper portion of the screen and pushes the output apparatus selection button to output the image to the designated output apparatus, the same as in FIG. 13 (Step S130).

Regarding the image outputted to a printer or to the host, a mark indicating completion of the output (output completion mark 29) is displayed near the image displayed on image display area 23 of image confirmation/output screen 21 or image list display sections 27a and 28a of output property screens 27 and 28.

When the end button is pushed, the screen goes back to the initial screen. However, regarding images which have not been outputted, the image data are arranged in the order to be outputted according to the format designated by the default output format button of image confirmation/output screen 21.

According to the image acquiring method and the display controlling program of this embodiment, in a display means of the control apparatus, displayed as three selectable modes are the pre-registration mode, where an image is acquired by radiographing, after correlation between body part information and a cassette, is registered previously as radiographing reservation information, the post-registration mode, where correlation between body part information and a cassette insertion order is registered as radiographing reservation information and an image is acquired, and the non-registration mode, where an image is acquired without registration of correlation as radiographing reservation information. Because a user can select a desired one from among the three, a system which is suitable for a large scale user, such as a large hospital, as well as a smaller scale user, such as a medical practitioner's clinic can be established.

In the above examples of the embodiment, it is structured that a desired mode is selected from among the three modes, namely the pre-registration mode, the post-registration mode and the non-registration mode. However, this invention is not limited to the above embodiments and it can also be other structures, such as a structure in which the desired mode is selected between the pre-registration mode and the non-registration mode, or a structure in which the desired mode is selected between the post-registration mode and the non-registration mode, as well as a structure in which the desired mode is selected from among more than three modes including modes other than the above-stated three modes.

Instead of the plate and the reader, an FPD (Flat Panel Detector) is available, and in this case, registration of the ID of the plate is replaced by registration of the ID of the FPD. The FPD returns image data with header information of its own ID to the controller, which correlates the accepted image data with the patient information by searching the ID as a key.

What is claimed is:

1. A medical image creating system without radiographing reservation information comprising:
   a cassette in which a recording medium is housed to record a radiographic image captured by radiographing a subject of a patient;
   a single radiographic image reading apparatus for the cassette; and
   a single control apparatus,
   wherein the single radiographic image reading apparatus and the single control apparatus are communicably connected with each other,
   wherein the single radiographic image reading apparatus comprises:
      a reading section for reading the recording medium in the cassette, and for creating image data of the captured image, and
   wherein the single control apparatus comprises:
      a storage section for storing image data of a plurality of captured images by collecting the image data of the captured image;
      a display section having a screen for displaying the plurality of the captured images;
      an image data selecting section for selecting image data of a plurality of images among the image data of the plurality of captured images, by selecting and displaying a plurality of images on the screen among the plurality of captured images;
      an examination information input device for inputting examination information including patient information of the patient after reading the captured image of the patient and displaying the plurality of the selected images; and
      a correlating device for collectively correlating the data of the plurality of the selected images with patient information of the patient inputted by the examination information input device, and
   a body part information input section having an radiographed body part selection area on the screen of the display section for inputting body part information; and
   an image adjusting section having an image processing condition adjustment area on the screen of the display section for adjusting an image processing condition of an image, wherein the display section displays simultaneously on the screen an image display area on which the plurality of the captured images are displayed, the radiographed body part selection area and the image processing condition adjustment area.

2. The medical image creating system of claim 1,
wherein the body part information input section displays a human body model in which a body part corresponding to the subject is selected in the radiographed body part selection area on the screen.

3. The medical image creating system of claim 1, further comprising:
a reading condition determining section for determining a reading condition based on the inputted body part information,
wherein the reading section reads the recording medium in the cassette according to the reading condition determined by the reading condition determining section.

4. The medical image creating system of claim 3, further comprising:
a processing device for processing the data of the plurality of captured images according to the inputted body part information,
wherein the correlating device correlates the data of the plurality of the selected images with the patient information, the data having been created by reading the recording media by the reading section according to the reading conditions based on the inputted body part information and having been processed by the processing device.

5. The medical image creating system of claim 1,
wherein the display section displays the plurality of the selected images simultaneously on the screen.

6. The medical image creating system of claim 1, further comprising:
an image adjusting section for collectively adjusting an image processing condition for the data of the plurality of the selected images.

7. The medical image creating system of claim 1, further comprising:
a first image processing device for processing the data of the captured image received from the single radiographic image reading apparatus according to the inputted body part information; and
a second image processing device for processing the data of the captured image processed by the first processing device, according to the image processing condition of the image,
wherein the display section displays the captured image processed by the first processing device or the first and the second processing devices on the screen.

8. A medical image creating method in which radiographing of a patient is conducted without radiographing reservation information to create a captured image of the patient by using a cassette in which a recording medium is housed and a medical image creating system in which a single radiographic image reading apparatus for the cassette and a single control apparatus are communicably connected with each other, the medical image creating method comprising the steps of:
recording a radiographic image captured by radiographing a subject of the patient onto the recording medium;
reading the recording medium in the cassette so as to create image data of the captured image by using the single radiographic image reading apparatus;
storing image data of a plurality of captured images by collecting the image data of the captured image;
displaying the plurality of the captured images on a screen;
selecting image data of a plurality of images among the image data of the plurality of captured images, by selecting and displaying a plurality of images on the screen among the plurality of captured images;
inputting the examination information including patient information of the patient in the single control apparatus after reading the captured image of the patient and displaying the plurality of the selected images; and
collectively correlating the data of the plurality of the selected images with the patient information of the patient, and
inputting body part information by a body part information input section having an radiographed body part selection area on the screen of the display section; and
adjusting an image processing condition of an image by an image adjusting section having an image processing condition adjustment area on the screen of the display section,
wherein an image display area on which the plurality of the captured images are displayed, the radiographed body part selection area and the image processing condition adjustment area are displayed on the screen of the display section simultaneously.

9. The medical image creating system of claim 7, further comprising:
a repeat mode setting section for implementing a repeat mode in which a same body part information inputted by the body part information input section is repeatedly applied to image data of every captured image to be read by the reading section or image data of every captured image to be processed by the first image processing device.

10. The medical image creating method of claim 8,
wherein in the step of inputting body part information, a body part corresponding to the subject is selected in a human body model displayed in the radiographed body part selection area on the screen.

11. The medical image creating method of claim 8, further comprising:
determining a reading condition based on the inputted body part information by a reading condition determining section,
wherein the recording medium in the cassette is read according to the determined reading condition.

12. The medical image creating method of claim 11, further comprising:
processing the data of the plurality of captured images according to the inputted body part information,
wherein the data of the plurality of the selected images is correlated with the patient information, the data having been created by reading the recording media by the reading section according to the reading condition based on the inputted body part information and having been processed in the processing step.

13. The medical image creating method of claim 8,
wherein the plurality of the selected images are displayed simultaneously on the screen of the display section.

14. The medical image creating method of claim 8, further comprising
collectively adjusting an image processing condition for the data of the plurality of the selected images by an image adjusting section.

15. The medical image creating method of claim 8, further comprising:
first processing the data of the captured image received from the single radiographic image reading apparatus according to the inputted body part information; and second processing the data of the captured image processed by the first processing device, according to the image processing condition of the image;

wherein the captured image processed in the first processing step or in the first and the second processing steps is displayed on the screen of the display section.

16. The medical image creating method of claim 15, further comprising:

implementing a repeat mode in which a same body part information inputted in the inputting step is repeatedly applied to image data of every captured image to be read in the reading step or image data of every captured image to be processed in the first processing step.

* * * * *